United States Patent [19]
Kim et al.

[11] Patent Number: 5,882,322
[45] Date of Patent: Mar. 16, 1999

[54] MEDICAL CASTS AND OTHER ORTHOPEDIC DEVICES COMPRISING THERMOPLASTIC THREE-DIMENSIONAL FIBER NETWORKS

[75] Inventors: Dai W. Kim, Chatham, N.J.; William E. Bessey, Charlotte, N.C.; John Nagel, North Plainsfield, N.J.; Gregory M. Clark, Weston, Conn.; Joseph S. W. Haas, Charlotte; Etheridge O. Oakley, Jr., Matthews, both of N.C.

[73] Assignee: Hoechst Celanese Corporation, Somerville, N.J.

[21] Appl. No.: 754,953

[22] Filed: Nov. 21, 1996

[51] Int. Cl.⁶ ........................................ B32B 1/00
[52] U.S. Cl. ............................. 602/6; 428/174; 428/175; 428/176; 428/178; 428/212; 428/225; 428/229
[58] Field of Search ................. 602/3, 6, 8, 46, 602/53, 60, 61, 62, 63; 428/174, 175, 176, 178, 212

[56] References Cited

U.S. PATENT DOCUMENTS

| | | |
|---|---|---|
| Re. 31,345 | 8/1983 | Swartzkopff et al. . |
| 2,029,370 | 2/1936 | Heldenbrand . |
| 3,219,514 | 11/1965 | De Roysancour . |
| 3,691,004 | 9/1972 | Werner et al. . |
| 3,691,570 | 9/1972 | Gaines et al. ........................ 5/347 |
| 4,128,684 | 12/1978 | Bomio et al. . |
| 4,212,692 | 7/1980 | Rasen et al. . |
| 4,252,590 | 2/1981 | Rasen et al. . |
| 4,516,572 | 5/1985 | Schlein . |
| 4,539,982 | 9/1985 | Bailly . |
| 4,584,228 | 4/1986 | Droste . |
| 4,631,221 | 12/1986 | Disselbeck et al. . |
| 4,672,005 | 6/1987 | Dyer . |
| 4,673,616 | 6/1987 | Goodwin . |
| 4,890,877 | 1/1990 | Ashtianizarandi et al. . |
| 5,158,821 | 10/1992 | Gebauer et al. . |
| 5,364,686 | 11/1994 | Disselbeck et al. . |
| 5,447,776 | 9/1995 | Desselbeck . |
| 5,455,060 | 10/1995 | Neamy et al. . |
| 5,480,708 | 1/1996 | Cheng . |
| 5,527,265 | 6/1996 | McKeel . |
| 5,540,964 | 7/1996 | Mallen . |

FOREIGN PATENT DOCUMENTS

| | | |
|---|---|---|
| 324714 B1 | 7/1989 | European Pat. Off. . |
| 0 326 285 A2 | 8/1989 | European Pat. Off. ........ A61F 13/04 |
| 0 356 078 A1 | 2/1990 | European Pat. Off. ........ A61F 13/04 |
| 356078 A1 | 2/1990 | European Pat. Off. . |
| 386864 B1 | 9/1990 | European Pat. Off. . |
| 0 401 580 A2 | 12/1990 | European Pat. Off. ....... D06M 23/14 |
| 386387 B1 | 5/1992 | European Pat. Off. . |
| 536 298 | 10/1931 | Germany .............................. D30/23 |
| 38 01 020 C1 | 7/1989 | Germany ...................... D06C 23/04 |
| 2 151 543 | 7/1985 | United Kingdom .............. B32B 3/06 |
| 2151543 | 7/1985 | United Kingdom . |
| WO 94/16657 | 8/1994 | WIPO ............................ A61F 13/04 |

*Primary Examiner*—Richard J. Apley
*Assistant Examiner*—Kim M. Lee
*Attorney, Agent, or Firm*—Alston & Bird LLP

[57] ABSTRACT

Cast padding materials and padding and lining materials for other orthopedic devices are made from three dimensional fiber networks which are semi-rigid and dimensionally stable. The fiber networks are made from textile fabrics that have projections and optional depressions which are compressible and return to their original shape after being compressed. The fiber networks are made by the thermo-mechanical deformation of textile fabrics that are in turn made from thermoplastic fibers.

21 Claims, 2 Drawing Sheets

MEDICAL CASTS AND OTHER ORTHOPEDIC DEVICES COMPRISING THERMOPLASTIC THREE-DIMENSIONAL FIBER NETWORKS

This is a continuation of U.S. application Ser. No. 60/009,057 filed Dec. 12, 1995.

RELATED APPLICATIONS

Commonly assigned U.S. Pat. No. 5,731,062, filed Dec. 22,1995; commonly assigned U.S. application Ser. No. 09/046,165, filed Mar. 23, 1998, which is a divisional U.S. Pat. No. 5,731,062, commonly assigned U.S. application Ser. No. 08/767,506, filed Dec. 16, 1996, now allowed, which claims the benefit of U.S. Provisional Application No. 60/009,143, filed Dec. 22, 1995; and commonly assigned U.S. application Ser. No. 08/770,026, filed Dec. 19, 1996, which claims the benefit of U.S. Provisional Application No. 60/009,061, filed Dec. 22, 1995, all contain related subject matter.

FIELD OF THE INVENTION

This invention relates generally to the field of orthopedic devices, and more specifically to the use of three-dimensional networks of thermoplastic fibers as the padding or lining material in an orthopedic device such as a cast or as the rigid cast itself.

BACKGROUND OF THE INVENTION

There is an ongoing need for materials that may be used in orthopedic devices to enhance the quality of life of users of the devices by providing orthopedic devices that are more comfortable and that allow more normal body movement. In particular, there is a need for materials that are lightweight, breathable, and comfortable when placed in contact with the skin or close to the skin for long periods of time underneath a rigid outer cast or other orthopedic device. Breathability is desirable because it facilitates drying and the elimination of perspiration. This leads to the faster healing of wounds and minimizes skin maceration. Materials that do not absorb and retain moisture when immersed in water are also desirable, because the casts or other orthopedic devices can then be worn while the patient is bathing. It is also desirable that the materials can be washed if they are in a device where they are accessible or can be removed. Cotton fabrics and the like that are often used retain water and are thus unsuitable for washing or for use in water.

With respect to medical casts, materials that are currently used under the casts are generally in the form of a gauze, which may be stretchable, and which is wrapped in multiple layers to the desired thickness. The materials inside the cast are most often made of cotton or synthetic fibers, such as polyester, rayon, or acrylic. Other materials that have been used or are currently in use include polypropylene, fluoropolymers (GORTEX®), and cellulose acetate. Cast padding materials based on these materials are difficult to dry, in some cases because of the inherent difficulty in drying the material (e.g. cotton, because it is hydrophilic), and also because the physical form of the material restricts the rapid removal of water by drainage and evaporation.

Many approaches have been taken to overcome the problems associated with perspiration and moisture underneath a cast. For example, U.S. Pat. No. 4,539,982 teaches odor absorbing webs that are composed of a foam or bundles of cellulosic fibers and that also include activated carbon particles for the purpose of absorbing moisture and odor. Perforated poly(vinyl chloride) foam that allows moisture to pass through the perforations and that can pass moisture along the surface is taught in U.S. Pat. No. 4,516,572. This material is dried by heating when it gets wet. U.S. Pat. No. 5,540,964 teaches cast lining materials which are made from hydrophobic fibers that have been modified so that their surface is hydrophilic. These can wick moisture away from the skin. U.S. Pat. Nos. 5,102,711 and 5,277,954 teach a breathable, layered combination of microporous films and open cell foams.

The materials in these patents all deal with eliminating perspiration and moisture by using materials that wick away or absorb moisture. None of these patents provide the materials in a form that is open enough to allow for easy "breathing" under the cast for rapid evaporation. It would be desirable to have a material that can be used under a cast that feels soft and that has an open structure so that air and water can pass through easily. Such a material would allow the easy removal of water and easy drying. It would also feel cooler and more comfortable because of better air circulation.

SUMMARY OF THE INVENTION

Three dimensional fiber networks as described below have the necessary breathability, light weight, and comfort that is needed for use as an inner layer in a medical cast and as a padding material in other orthopedic devices. The breathability also allows faster drying of the material through evaporation and drainage. The fiber networks can also be used in a somewhat more rigid form as soft supporting casts without a rigid outer cast or as a structural member in an orthopedic device. The three dimensional fiber network structures that are used in medical casts and other orthopedic devices are semi-rigid and dimensionally stable, but have sufficient flexibility to be useful as cushioning materials. The fiber network structures are generally compressible, and when the compressive force is removed, the materials return to their original shape (i.e. they are resilient). These fiber network structures comprise filaments that are made of a thermoplastic polymer or copolymer, or a polymer blend or alloy, and do not include a rigid thermoset polymer. Usually, the filaments are made of a single thermoplastic polymer or copolymer. The filaments may also be made by the coalescence of more than one small diameter filament, in which case there may be more than one kind of polymer. The networks comprise a multiplicity of projections rising from the plane of the textile fabric from which the fiber network is made. Projections are portions of the textile fabric that rise above the base plane, generally in an abrupt way. Depressions, which are projections on the opposite side and in the opposite direction from the base plane, may optionally also be present. The projections and optional depressions have retained an open fabric-like appearance, consisting of discrete filaments or bundles of filaments which are generally not bonded at the intersections where the individual filaments cross over one another. There may be bonds at the intersections if the attachments are elastic or easily broken when the network is initially compressed (i.e. they are not "tightly bonded") after which the network becomes resilient. The network is "resilient" if the projections and optional depressions substantially recover their shape after being compressed to 50% of their height. This means that there may be minor changes in the shapes of the projections and optional depressions, as for example a change in the curvature of the edges at the top of the projection. As the density of tight bonds at the points at which the fibers cross over one another increases, the fiber network structure and the projections become more rigid, and the projections lose their resilience. Because of the open structure of the textile fabric and the large void volume within the projections and/or depressions, the network has a low density compared with the polymer (generally less than about 10%, preferably less than about 5%) based on the amount of space occupied by the network. Air and other fluids can flow through the fiber network structure with little resistance. As a result, materials comprising the fiber network that are used under the cast or elsewhere in an orthopedic device are breathable and therefore dry easily.

The filaments in the formed fiber network may be in the form of a monofilament generally having a diameter of at least about 0.1 mm, corresponding to about 100 dpf in the case of poly(ethylene terephthalate). The filaments used in the fiber networks can also be derived from multifilament yarns having approximately the same total diameter, including hybrid yarns and yarns that include bicomponent fibers, where the individual filaments of the yarns have coalesced to larger filaments under heat and pressure during the shaping process. Alternatively, the filaments may be individual filaments in a multifilament yarn in which the individual filaments have not coalesced together. In this case, the individual filaments will generally have a denier of at least 1 dpf and preferably less than or equal to 16 dpf, although there may be examples where the filaments in a multifilament yarn may be as large as 100 dpf. Projections made from multifilament yarns using 1–16 dpf filaments are significantly softer than projections made from monofils. Generally, the bundles of yarn in the multifilament yarn using 1–16 dpf filaments have a diameter greater than about 0.1 mm in order to give the formed fiber network sufficient strength to support a cast. The projections of the products made using multifilament yarns having small individual filaments that have not been coalesced may be made more rigid by including a small amount (up to about 25% by weight, preferably 0.1% to 10% by weight) of a resin that holds the individual filaments together and makes the bundles of filaments behave more like single filaments having a larger diameter. The added resin may be an adhesive or a resin that sets by crosslinking, such as a flexible thermoset.

The fibers utilized in formed fiber networks for medical casts and other orthopedic devices are made of a thermoplastic polymer or copolymer (or optionally a blend or polymer alloy) that generally melts at a temperature in the range of about 80° C. to about 375° C. Generally, a single polymer or copolymer is used to make the individual fibers. As stated earlier, the filaments may also be made by the coalescence of the individual filaments of a hybrid yarn, a bicomponent fiber, or a multifilament yarn, though these are less preferred. The polymer is preferably made into fiber by a melt spinning process. Preferred classes of polymers that may be made into three dimensional fiber networks in general include polyesters, polyamides, thermoplastic copolyetherester elastomers, poly(arylene sulfides), polyolefins, aliphatic-aromatic polyamides, polyacrylates, and thermotropic liquid crystalline polymers. For medical casts, the preferred class of polymer is polyesters, with poly(ethylene terephthalate) being most preferred.

The three-dimensional fiber network structure is generally made by deforming a textile fabric, which may be a fabric made from a monofil or from a multifilament yarn, into the desired shape at a temperature high enough that the fibers can be permanently deformed, as would occur, for example, in a fiber drawing process. The fiber temperature will generally be above the glass transition temperature (Tg), and, will also be below the melting temperature. The deformation is brought about using a thermomechanical process, which means the application of a mechanical force at an elevated temperature. The mechanical force can be applied using numerous methods, such as solid phase pressure forming, vacuum bladder match plate molding, interdigitation, deep drawing, use of a heated mold, and the like. Heat and pressure are applied for a sufficient time that the textile fabric is permanently deformed, but not for such a long time or at such a high temperature (e.g. well above the melting temperature) that the filaments coalesce, causing the shaped fiber network to lose its open net-like structure and resilience. The individual filaments in the three-dimensional fiber network structure still have retained much of their individual fiber-like appearance and properties. If a multifilament yarn is being made into a formed fiber network and the fibers are not being condensed into larger filaments by a melting process, it may be advantageous to use a yarn that is partially drawn, and thus partially oriented, rather than a yarn that has been fully drawn and oriented to maximize tensile properties. Such a yarn is generally known as a partially oriented yarn, referred to by such acronyms as POY, LOY, or MOY. Partially oriented yarns are more readily deformed into three dimensional formed fiber networks than are more fully drawn yarns. Three dimensional formed fiber networks that are made from multifilament yarns are described in German Patent DE 3801020C1 and U.S. Pat. No. 5,158,821. As stated previously, these may be made stiffer by including up to 25% of a resin (e.g. an adhesive or a flexible thermoset).

The starting two-dimensional textile fabric that is utilized in making the three-dimensional fiber network for use in casts is selected from the standard classes of textile fabrics, such as knit or woven, textile fabrics. The type of fabric depends on the kind of resulting network structure that is desired. Knit fabrics have the advantage that their structure is readily deformed without excessive elongation of individual fibers, which leads to breakage of the fibers. Knits are also more flexible and conform to the body when used as a wrap. Woven fabrics have the advantage that they are more readily produced from larger diameter fibers, such as monofils. Wovens are more dimensionally stable and easier to use when attached to a preformed brace. Wovens also can be made stiffer and therefore can contribute to stabilization.

Non-woven fabrics may also be used, although they are less preferred, because the individual filaments are bound to one another as part of the manufacturing process. Non-wovens having larger diameter filaments (at least 0.1 mm in diameter) will be more rigid because of the bonding between the filaments, and will also be difficult to shape from a flat fabric. A non-woven would generally be manufactured by a process whereby the non-woven fabric is made with the pattern of projections in the material as it is made, as for example by making the non-woven on a plate or belt having projections in it.

The expression "orthopedic devices" as used herein refers to orthopedic devices for bracing and fixation, where bracing means support braces that allow some mobility, as in a joint, and where fixation means immobilization, as in a medical cast. The orthopedic devices that utilize the materials taught herein are used externally. Such orthopedic device are in close contact with the skin, and padding materials are needed in such devices. An important end use of the materials is padding for medical casts.

From the disclosure above, it should be clear that the word "filament" as applied to the three-dimensional product includes continuous lengths of fibrous material that are themselves made from smaller diameter filaments that have been bound together during the manufacturing process, and not just filaments that have been extruded during a spinning process.

DETAILED DESCRIPTION OF THE INVENTION

The three-dimensional fiber networks that have particular utility as cast padding materials for orthopedic devices, and in particular medical casts, are made up of a multiplicity of projections on the plane of the textile fabric from which the network is made. Depressions may optionally also be present on the opposite side of the fabric from the projections. Examples of rigid three-dimensional fiber networks and methods of making them are summarized in U.S. Pat. Nos. 5,364,686 and 4,631,221. The projections and optional depressions can be in the shape of cones or truncated cones, pyramids or truncated pyramids having polygonal bases, cylinders, prisms, spherical elements, and the like. Generally, the apex points or surfaces of the projections define a plane parallel to the base plane. Similarly if there are also depressions, their apex points or surfaces define a second surface, such as a plane parallel to the base plane. As a result, the preferred three-dimensional networks define two surfaces or planes, one being defined by the tops of the projections and the other being defined by either the base plane or the plane or surface defined by the depressions. Furthermore, the projections and optional depressions are generally arranged in a uniform or repetitive pattern with a uniform spacing. However, the shapes, heights, sizes and spacings of the projections and optional depressions can be modified to suit the specific application and to conform to a specific shape. The projections and/or depressions can also be elongated along one direction of the plane, and in the extreme case, can run the entire length or width of the textile, in which case the projections are really corrugations, like those typically seen in cardboard. Non-corrugated structures are preferred for most cast padding or lining applications. However, as explained in Example 11, corrugated structures that exhibit rigidity in one direction while retaining flexibility in a different direction can be used to make semi-rigid casts, splints, or stabilization in devices.

Figure 1:
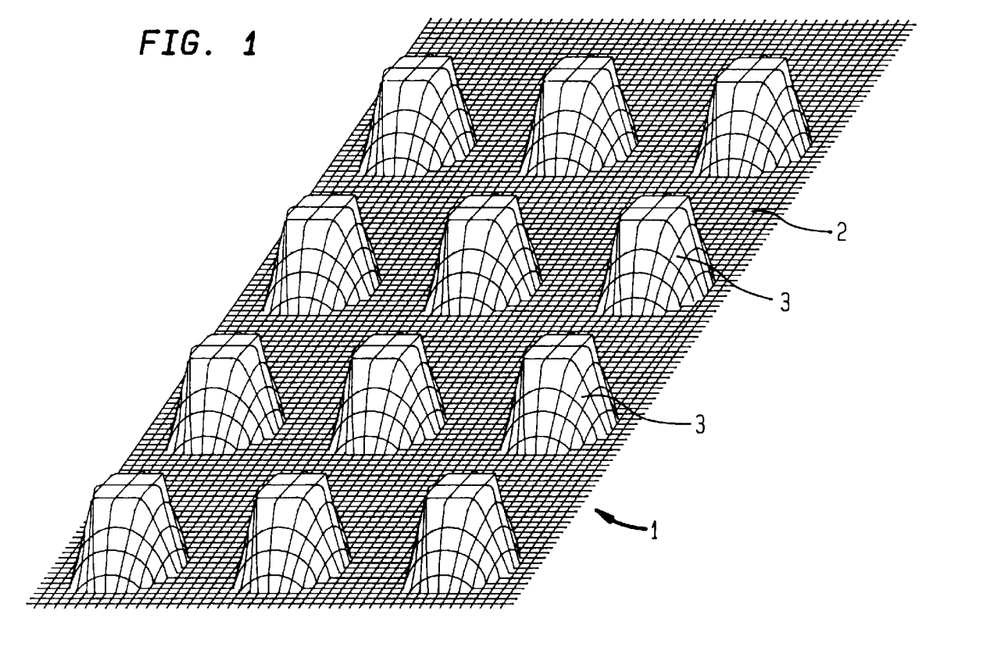
FIG. 1 shows schematically a section of a three-dimensional fiber network structure 1 having a multiplicity of "hat-shaped" projections 3 on base area 2. The open mesh structure of the fiber network is illustrated. These illustrative hat-shaped projections have a square base and square top, with the top having smaller dimensions than the base.
Figure 2:
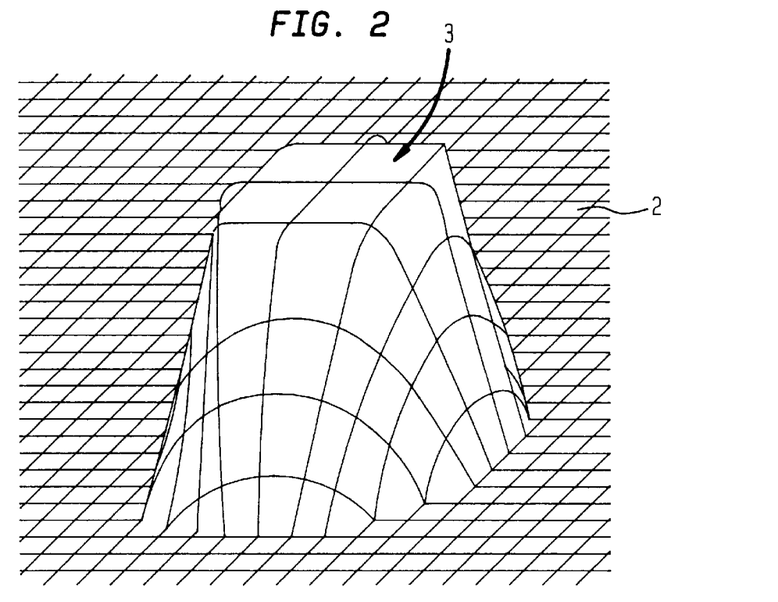
FIG. 2 schematically depicts an enlargement of one of the hat shaped projections 3 of FIG. 1, showing the widening of the mesh structure of the textile material which occurs in the area that is deformed.
Figure 3:
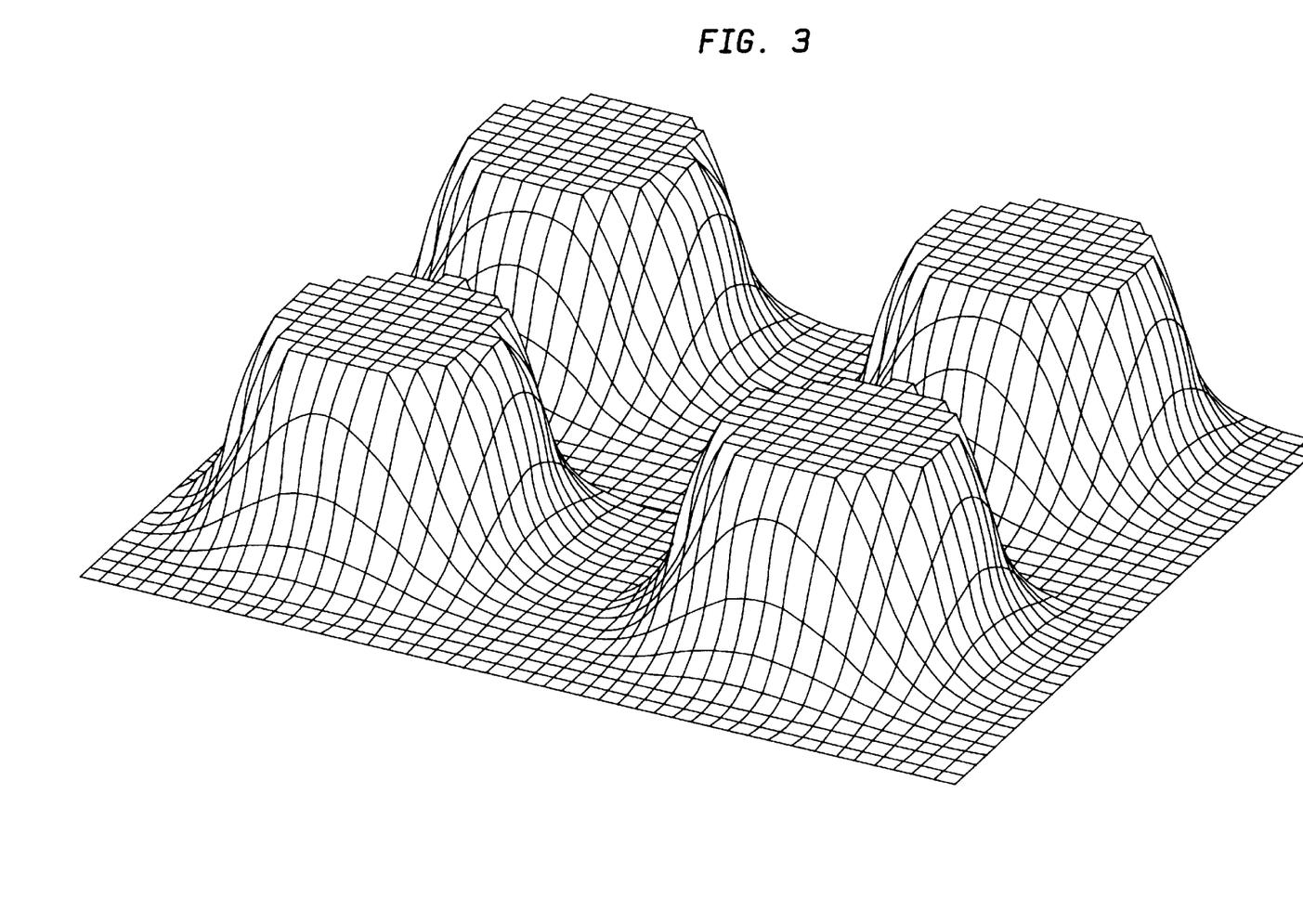
FIG. 3 schematically depicts an enlargement of four projections that are in the shape of truncated cones.

The sizes, heights, shapes and spacings of the pattern of projections and depressions affect the cushioning properties and "feel" of the three-dimensional networks. The rigidity of the individual fibers in the network structure also is a major factor in determining the cushioning properties of the three-dimensional networks, and the rigidity of the fibers in turn depends on the diameter of the filaments and the kind of materials (e.g. polymers) from which the filaments are made. For most applications in casts and other orthopedic devices, filament diameters are in the range of about 0.1 mm to about 0.25 mm. An example of a preferred structure of regularly spaced projections having a square base and a square top that has shorter sides than the base is shown in FIG. 1. Another more preferred structure consists of a regular array of projections which are truncated cones of similar size and shape, as shown in FIG. 3, for example.

The polymers used as filaments in the three-dimensional fiber networks for use in medical casts and other orthopedic devices are preferably made of a thermoplastic polymer rather than composites of a reinforcing fiber and a matrix polymer, such as a thermoset, which have been utilized previously for making rigid networks. The polymers may include minor amounts of additives, such as flame retardants, spinning lubricants, and the like. The thermoplastic polymers generally have a melting temperature in the range of about 80° C. to about 375° C., preferably about 140° C. to about 350° C. Thermoplastic polymers that may be used for making three dimensional fiber networks in general include: (1) polyesters of alkylene glycols having 2–10 carbon atoms and aromatic diacids. Poly(alkylene terephthalates), especially poly(ethylene terephthalate) and poly(butylene terephthalate), are particularly preferred. Also preferred are poly(alkylene naphthalates), which are polyesters of 2,6-naphthalenedicarboxylic acid and alkylene glycols, as for example poly(ethylene naphthalate); (2) thermoplastic copolyetherester elastomers, described in more detail below; (3) polyamides, especially nylon 6 and nylon 66, which are commonly used in making fibers; (4) poly (arylene sulfides), especially poly(phenylene sulfide); (5) polyolefins, particularly polyethylene and polypropylene; (6) aliphatic aromatic polyamides, such as polyamides derived from terephthalic acid and 2-methyl-1,5-pentanediamine; (7) polyesters derived from 1,4-cyclohexanedimethanol and terephthalic acid; and (8) thermotropic liquid crystalline polymers, such as for example polyesters derived from 6-hydroxy-2-naphthoic acid and 4-hydroxybenzoic acid.

Specific preferred polymers for medical cast liners include poly(ethylene terephthalate) (PET), thermoplastic copolyetherester elastomers, nylon 6 and 66, poly(ethylene), and polypropylene. Thermoplastic copolyetherester elastomers are available from a number of manufacturers, including Hoechst Celanese Corporation, Somerville, N.J., under the RITEFLEX® trademark. PET is the most preferred polymer for use under medical casts. PET is widely available from many manufacturers, including Hoechst Celanese Corporation, Somerville, N.J. The PET should be of high enough molecular weight to be suitable for spinning into fibers; generally a molecular weight corresponding to an intrinsic viscosity (I.V.) of at least about 0.6 dl/gm is suitable, where the I.V. is determined by measuring the relative viscosity of a 4% solution (weight/volume) in o-chlorophenol at 25° C. The relative viscosity is then converted to intrinsic viscosity. Polypropylene and nylons are also widely available from many manufacturers.

The spacing, size, height, and shape of the projections and optional depressions, the diameter of the filaments, and fabric construction of the three dimensional fiber networks are chosen to give the desired properties (e.g. cushioning, breathability) for the specific application. The shapes of the deformations are determined by the process used to make them. For example, in a deformation process in which the textile fabric is held against a plate with round holes and a cylindrical rod is pushed through the hole on the same side as the textile fabric, so that the textile fabric is pushed through the hole, the projections that are made in the textile fabric will be in the shape of truncated cones (i.e., the base and top of the projections will both be round), with the diameter of the top of the cone being the diameter of the rod that pushes the textile through the hole. Similarly, if a plate with square holes and a rod with a square cross section is used, the projections will be "hat-shaped".

The fiber networks described herein are lightweight, durable and breathable. They are springy and resilient, which means that they can be compressed (preferably repeatedly) without a significant loss in properties. Depending on the stiffness of the fibers and the sizes of the projections, they may be used as cushioning materials, as impact absorbing materials, or as semi-rigid support materials. Because they are generally made of only one polymer, preferably PET, they can be easily recycled after use with other recyclable plastics, (e.g. bottles in the case of PET). The fiber network materials can be used as single layers, they can be nested face to face, with the projections interlocking, or they can be stacked with the projections of one layer against the base plane of the next layer or with the base planes of the two layers against each other to provide thicker spacers and cushions. The materials having more than one layer can be bonded together by such methods as adhesive bonding or ultrasonic welding. The fact that the projections can interlock in face to face nesting or can fit together when the base plane of one layer lies on top of the projections of the next lower layer gives the fiber networks a self-sticking property when they are being wrapped around an arm or leg for use in a cast padding. This makes the application of the cast padding materials to an injured arm, leg, or other body part easier. Because of the stiffness of the filaments, the cut edges "stick" to other layers of material. This also gives the three-dimensional fabric a self-sticking feel.

The invention is further illustrated by the following non-limiting examples.

EXAMPLES

Example 1

RITEFLEX®640 copolyetherester elastomer having a melting temperature of about 180° C., obtained from Hoechst Celanese Corporation, was melt spun to yield a 0.20 mm (435 denier) monofil having the following properties. The fiber tenacity was measured by ASTM Test Method D-3822 as 2.8 gpd, with 98% elongation at break. The elastic recovery of the fiber was measured by the same test method as 100% after 100 cycles at either 20% or 50% elongation. The monofil was knitted into a textile fabric having a wale of 8 wales/inch and a weft of 42 course/inch.

The knit fabric was shaped into a three-dimensional structure by using a heated press plate. The press plate was a metallic plate having ⅜ inch diameter holes, and was heated to about 160°–230° C. The fabric was pressed against the heated plate for 9 seconds, and pins that were ¼ inch in diameter were then pushed through the holes. This yielded truncated cone shaped projections on the fabric which were about ⅜ inch in diameter at the base and ¼ inch in diameter at the top. The projections were about 3/16 inches in height and were spaced in a square grid array with the nearest distance between the projections (center to center) being about ¾ inch.

This shaped fiber network had a soft springy feel and could be repeatedly compressed without a loss of springiness.

Example 2

RITEFLEX®672 thermoplastic copolyetherester elastomer, which melts at about 205° C., was obtained from Hoechst Celanese Corporation, and was melt spun into 823 denier monofil (about 0.28 mm in diameter). The tenacity at break of the fiber was 2.4 gpd, and it had an elongation at break of 87%, as measured by ASTM Test Method D-3822. The elastic recovery of the fiber, measured by the same method, was 100% after 100 cycles at either 20% or 50% elongation.

The fiber was knitted into a fabric having the same wale and weft as that in Example 1. The fabric was deformed into a three-dimensional network using the press plate apparatus of Example 1 under the same conditions as in Example 1. This shaped fiber network also had a soft springy feel and could be repeatedly compressed without a loss of springiness.

Example 3

Commercial PET that was made for use in textile fabrics was melt spun into a 0.182 mm monofil (about 321 denier). The monofil was then made into a plain knit fabric with 16 wales and 24 courses per inch.

The fabric samples were deformed into a three-dimensional network using a similar kind of apparatus as described in Example 1, but having ¼ inch holes in the press plate and ⅛ inch diameter cylindrical pins to yield conical projections with flat tops. The base and tops of the projections were the same as the diameter of the holes in the base plate and the diameter of the pins. The projections were arranged in a square grid array and were separated by ½ inch (center to center). The height of the projections was about ¼ inch. The projections were made by heating the base plate and the pins to 240° C. and pressing the fabric through the holes for about 30 seconds. The deformed fabric was resilient and had a comfortable, springy feel when pressed down by hand, and retained its feel even after multiple compressions. A sample of this material in the form of a 3 inch×12 foot tape was tested as the padding material for a short arm cast. The cast was worn in the shower and while swimming. The cast dried much faster than the traditional gauze cast padding material and was judged to be much more comfortable.

Example 4

A series of poly(ethylene terephthalate) (PET) fabric samples (both knit and woven) were made into three dimensional fiber network materials by the method of pressing the fabric against a heated base plate having a square grid array of evenly spaced holes at about 200° C. for two minutes and then pushing the fabric through holes in the base plates using cylindrical pins that were heated to about 180° C. The pins were kept in place (projected through the holes at temperature) for 15 seconds before being withdrawn, except in Sample No. 4 (below), where the pins were kept in place for 600 seconds. This resulted in three-dimensional networks of cone-shaped projections with flat tops which were evenly spaced and in which the bases of the projections had the diameter of the holes and the tops of the projections had the diameter of the pins. The heights of the projections (the thickness of the samples) was somewhat less than the depth of the penetrations through the holes by the pins due to shrinkage after the mechanical force was removed. Both knit and woven fabrics were tested.

These samples were subjected to compression tests using a modification of methods that are used for polyurethane foams and latex foams. Samples of the materials were placed between the plates of an Instron tensile tester and then pre-loaded to a load of 0.02 psi. The distance between the plates at 0.02 psi of compression was defined as the thickness of the sample. The samples were then compressed to 60% compression for two cycles at test speeds of 0.2 in/min for samples 0.10–0.29 inches in thickness, 0.5 in/min for samples 0.30–0.69 inches in thickness, and 1.0 in/min for samples 0.70–1.39 inches in thickness. The two pre-cycles above made a significant change in two of the samples (Nos. 4 and 6 in Table 1); the precycling measurements are also reported for these two samples. Six minutes after the precycling above, a compression test was run to 60% compression at the same speed as in the pre-cycling. Stress and percent compression were measured, and the stress at 25% and 50% compression was measured. These values are recorded in Table 1, along with the averages for runs where there were duplicate measurements. These measurements show an increase in stress with increasing compression, which is a characteristic that is desirable for cushioning applications.

The apparent volume was computed based on the thickness as measured at 0.02 psi above and the measured dimensions of the sample. This was used to compute the apparent density, which ranged from 0.016 to 0.067 gms/cc. By comparison solid PET has a density of about 1.4 gms/cc. Thus the apparent density of the three dimensional fiber network is less than about 5% of the density of solid PET (1.1%–4.8% in these examples). The apparent densities of the samples in gms/cc are also listed in Table 1; these can be converted to pounds/cu. ft. by multiplying by 62.4.

Possible orthopedic applications of these sample are as follows: Knit samples (Samples 3, 4 and 7) may be used as cast padding. Samples 1 and 5 may be used as a brace lining. Samples 2 and 6 may be used as stabilization devices.

Example 5

A cast typically comprises three layers. The inner layer (the lining) is a stockinette material of the type that is in contact with the skin in conventional cast designs. The second layer (the padding layer) comprises the three dimensional fiber network. The fiber dimensions and the shapes, sizes, heights and spacings of the projections are selected to provide support and comfort to the wearer of the cast. Projections 3–6 mm in height and 8–12 mm in diameter arranged in a square grid array with a center to center spacing of 10–15 mm are preferred for this application. Generally, the projections point away from the body part, because the base plane of the fabric has a more comfortable feel to the skin than the tips of the projections. The outer layer is a conventional cast material, such as fiberglass or plaster. Such a cast is much more breathable than casts using current materials, especially if the outer layer is also porous (e.g. fiberglass). The cast can also be constructed without the stockinette, so that the three dimensional fiber network is directly against the skin and acts as both the lining and the padding layer.

Example 6

Sheets of the fiber network can be precut into shaped forms for specific kinds of applications, and the precut forms may furthermore be supplied with fasteners, such as VELCRO™ fasteners. Sheets or rolls of the material may also be cut and shoped by the end user, such as a physician or consumer. Examples of precut forms include forms that are shaped for knees, ankles, and elbows. The material may also be supplied as rolls of batting of various lengths and widths for specific applications. The batting may optionally be supplied with VELCRO™ or other fasteners. The fasteners may be at the ends of the rolls or along the sides of the rolls, or both, depending on the specific end use.

A piece of material having the approximate dimensions of Example 12 was cut into an 8"×8" square, which was further shaped to fit under a wrist brace. After several months of wear, a test subject found this material to be extremely comfortable.

Example 7

The three dimensional fiber network may be modified from the material described above in that the fibers in the projections are bonded together at the points where the fibers cross over one another. Bonding can be carried out by numerous methods, such as ultrasonic welding. The projections become rigid because of the bonding at the crossover points. The fabric in the base plane is still unmodified and is thus still flexible. The resulting modified fiber network is a network of rigid spacers that are mounted on a flexible net fabric. This enhances the conformability of the fiber network to the contours of the body. As a result, the material can be applied with a minimum of custom cutting (i.e., fewer or no pleats are needed). Such a material is also very drapable and may be useful in other applications as well, such as apparel (i.e. clothing).

For example, the three dimensional fiber network is first modified as described above by ultrasonic welding of the projections. The fiber network is then wrapped around the part of the body that is to be placed in a cast, with the fabric side down and the rigid domes (projections) facing up. A soft liner (e.g. a knit liner) may optionally be placed between the skin and the fiber network for even greater comfort. A cast or other rigid structure is then placed on top of the rigid projections to create a cast with a breathable spacing layer.

Example 8

Traditional stockinette material used in casts is made of stretchable net material that is shaped like a tube sock without a toe. Material that can be used in a stockinette, such as knit poly(ethylene terephthalate, can be shaped to become a formed fiber network in stockinette form. Processes can be envisioned in which a knit fabric in the shape of a tube is treated by a thermomechanical process whereby an array of projections and/or depressions is made on the tube. Alternatively, flat material having the projections and/or depressions can be cut and sewn to form the tabular product having projections and/or depressions. The stockinette tube with the outward projections can be slipped onto an arm or leg to provide a stockinette with resilient, flexible spacers. This results in a breathable cast once a hard cast is placed over the stockinette.

Materials that can be used to make the tube of material having projections and/or depressions include poly(ethylene terephthalate) and thermoplastic copolyetherester elastomer. Poly(ethylene terephthalate) is the most preferred polymer.

Example 9

Two pieces of a formed fiber network are nested together so that the projections face inward toward each other and the base surfaces of the fabrics that were used to make the fiber network face outwards. In this way, more fabric is placed against the skin and also against the cast, providing for greater support and comfort. The projections in the formed fiber network materials are readily arranged and shaped so that they naturally interlock when the surfaces with the projections face one another (e.g. triangular shaped projections and triangular shaped spaces between the projections). The fiber network can also be made to interlock with other materials, such as a thick fabric that has holes that match the arrangement of the projections. Finally, the fiber network can be wrapped around upon itself, with the projections of one layer nesting inside the projections of the next layer, making the wrapping with overlap at the edges easier and more comfortable. The edges of the fiber network material, because of the large fibers, stick to other layers of the material, giving the fiber network a self-sticking feel when wrapped around an arm, leg, or the like with overlapping layers.

Example 10

The projections may also be elongated, and in the extreme case can run the entire length or width of the fabric, giving the projections the appearance of corrugations, like those in cardboard. Such materials are extremely useful in applications where stiffness is required in one direction while flexibility is required in the other direction. These materials are useful, for example, as splints, semi-rigid casts, or other stabilization devices, because the materials are easily wound around a limb, but cannot easily be bent perpendicular to the direction of the corrugations. For example, knee and wrist splints use the corrugated formed fiber product with the corrugations running parallel to the leg or arm. Such devices offer the needed support, but because they have the open structure of the fiber networks, they are very breathable, comfortable, and do not retain water.

Example 11

The three dimensional fiber network can be used as the padding layer or liner of a removable cast for the foot, knees, and other parts of the body. Conventional removable casts and other devices used a liner comprised of polyurethane foam with fabrics laminated to both surfaces. A removable lower leg and foot cast was modified by replacing the foam lining with a three-dimensional fiber network as the lining material. The liner was easily washed and was durable, and could be removed for replacement or laundering.

Many of the synthetic fabrics used in making three dimensional fiber networks, such as polyester, do not support the growth of bacteria. Synthetic fabrics may also be made that incorporate bacteriacide. The materials also do not degrade, tear, or absorb water. The shoe cast is in the shape of an open toed shoe, and is designed to be easily put on the foot and removed through the use of fasteners, such as VELCRO™ fasteners. Removable casts for other parts of the body can also be designed similarly, with three dimensional formed fiber product as the padding layer. Alternatively, more rigid three dimensional formed fiber products can be used as a fixed or removable cast.

Example 12

Formed fiber product having the following approximate dimensions is particularly suitable in rolled form as a cast padding material. A 0.15 mm diameter PET monofil (about 220 denier) is knit into a plain jersey knit fabric having about 17 wales/inch and about 38 courses/inch and a weight of about 3 ounces/square yard. The fabric is formed into a product having domes about 4–5 mm high and 9–10 mm at the base, and arranged in a square grid array with a center to center spacing of about 13 mm.

Example 13

A poly(ethylene terephthalate) (PET) product as described in Example 12 was subjected to a series of tests to determine its suitability as a padding material to be used under casts. The test data for this sample are presented in Table 2. Tests were also carried out on other commonly used materials and commercial products for comparision. The comparative samples include a fluoropolymer membrane layered with polyurethane foam and a needle-punched non-woven fabric. The product of Example 12 generally performed better than the other samples that were tested. The tests and test methods are explained below.

Saturation Moisture Pickup

This test measures how rapidly a material dries after it is immersed in water. A 3 inch by 4 inch sample of material is clipped to a balance that is capable of weighing suspended samples. The weight of the sample is measured and is recorded as the dry weight ($W_{dry}$). The sample is then immersed in water until it is saturated by raising a beaker of water around the suspended sample. The water is then removed. Water initially drips from the sample at a rapid rate but then slows down. When the rate of the dripping is less than 1 drop every 5 seconds, the sample weight is again recorded. This weight is defined as the weight of a saturated sample ($W_{sat}$). The time that was required for the rate of dripping to decrease to less than 1 drop every 5 seconds after the water was removed is the drip time. The weight of the saturated sample is monitored. The time required for the sample to go from saturated weight back to dry weight is measured and is the drying time. The moisture pick-up is the % difference between the saturated weight and dry weight ($100\% \ (W_{sat}-W_{dry})/W_{dry}$).

Convective Cooling Test

This test measures the retardation of cooling of a heated chamber of a two chamber test apparatus from about 45° C. to room temperature when the two chambers are separated by a single layer of padding material. Faster cooling rates show that body heat is dissipated from the skin faster, which results in greater comfort. The test apparatus has two adjacent chambers, one above the other, separated by a 3"×4" rectangular opening. The dimension of each chamber is approximately 1'×1'×1' Each chamber contains a thermocouple. The apparatus is heated with a heat gun until the thermocouple in the lower compartment reaches a temperature of about 45° C., which is recorded as the starting temperature ($T_{start}$). A 3"×4" sample of the material being tested is placed in a sample tray across the opening between the two chambers. A heat gun that blows ambient air into the upper half of the test chamber is turned on, and a chronometer is started at the same time. This is the start of the test. The two thermocouples in the two chambers (one above and one below the sample) are monitored. When the bottom thermocouple reaches ambient temperature (about 23° C.) or both thermocouples reach the same temperature, the experiment is complete, the chronometer is stopped, and the temperature is measured ($T_{stop}$). The cooling rate is ($T_{start}-T_{stop}$)/$t_{test}$, where $t_{test}$ is the duration of the test as measured by the chronometer. To correct for variability in conditions, the experiment is run once without a sample. The cooling time without a sample (8 minutes in this case) is subtracted from each cooling time with a sample. The corrected cooling times are reported in Table 2.

Air Permeability

This test was run generally according to ASTM test method D-737-75 to determine how permeable this and other padding materials are to the flow of air. The standard pressure drop in these tests was 0.5 inches of water. Because the samples of this invention are more permeable than provided for in the test method, the orifice diameter for these samples was reduced from 2.75 inches to 1.75 inches. The measured value was then corrected by multiplying by the ratio of the areas (2.47).

Water Permeability/Batheability

This test is designed to determine the rate at which water can be flushed between a hard cast and a patient's limb using the padding material taught herein. Two 10 inch long tubes are placed in concentric arrangement so that there is an annular region between the outside of the inner tube (2.5" diameter) and the inside of the outer tube (2.6" inner diameter). The outer tube can be opened in a clamshell fashion to facilitate testing. Three feet of padding material is wrapped around the inner tube and the outer tube is then placed over it, and closed and sealed. The annulus remains open at both ends. The assembly is mounted vertically and water enters at the top under a pressure head of 20 cm of $H_2O$. Enough water is passed through the system to saturate the padding material. The time to pass an additional 7 liters of water through the annulus is then measured, and the flow rate is computed in liters/minutes.

It is to be understood that the above embodiments of the invention are illustrative only, and modification throughout may occur to one skilled in the art. Accordingly, this invention is not to be regarded as limited to the embodiments disclosed herein.

TABLE 1

Compression Tests

| Sample No. | Fabric Type[1] | Penetration (inches) | Fiber Diameter (mm) | Measured Thickness[2] (inches) | Network Spacings[3] (inches) | Apparent Density (gms/cc) | Specimen No. | Stress @ 25% Compression (psi) | Stress @ 50% Compression (psi) |
|---|---|---|---|---|---|---|---|---|---|
| 1 | Woven 37 × 37 | 0.313 | 0.25 | 0.195 | ½ × ¾ × 1 | 0.047 | 1 | 1.07 | 1.73 |
|  |  |  |  |  |  |  | 2 | 1.11 | 1.73 |
|  |  |  |  |  |  |  | avg | 1.09 | 1.73 |
| 2 | Woven 20 × 20 | 0.313 | 0.40 | 0.200 | ½ × ¾ × 1 | 0.065 | 1 | 2.22 | 3.26 |
|  |  |  |  |  |  |  | 2 | 2.32 | 3.37 |
|  |  |  |  |  |  |  | avg | 2.27 | 3.31 |
| 3 | Knit | 0.363 | 0.20 | 0.345 | ½ × ¾ × 1 | 0.023 | 1 | 0.27 | 0.79 |
|  |  |  |  |  |  |  | 2 | 0.29 | 0.83 |
|  |  |  |  |  |  |  | avg | 0.28 | 0.81 |
| 4 | Knit | 0.563 | 0.20 | 0.495 | ½ × ¾ × 1 | 0.016 | 1 | 0.53 | 0.90 |
|  |  |  |  |  |  |  | 2 | 0.55 | 0.90 |
|  |  |  |  |  |  |  | 3 | 0.82 | 1.00 |
|  |  |  |  |  |  |  | —[4] | — | — |
| 5 | Woven 37 × 37 | 0.188 | 0.25 | 0.140 | 1/4 × 3/8 × ½ | 0.064 | 1 | 5.44 | 8.01 |
|  |  |  |  |  |  |  | 2 | 5.68 | 9.09 |
|  |  |  |  |  |  |  | avg | 5.56 | 8.55 |
| 6 | Woven 20 × 20 | 0.188 | 0.40 | 0.193 | 1/4 × 3/8 × ½ | 0.067 | 1 | 13.73 | 23.45 |
|  |  |  |  |  |  |  | 2 | 20.21 | 34.07 |
|  |  |  |  |  |  |  | —[5] | — | — |
| 7 | Knit | 0.313 | 0.20 | 0.195 | 1/4 × 3/8 × ½ | 0.040 | 1 | 1.11 | 2.98 |
|  |  |  |  |  |  |  | 2 | 1.11 | 3.04 |
|  |  |  |  |  |  |  | avg | 1.11 | 3.01 |

[1] The knit fabrics were a plain Jersey knit having approximately 17 wales/inch and approximately 38 courses/inch. For the woven fabrics, the units are given in yarns per inch.
[2] At 0.02 psi
[3] Diameter at top of projection × diameter at bottom of projection × spacing (center to center), in inches.
[4] Pre-cycling significantly changes load curve characteristics. Specimens #1 and #2 were run with pre-cycling. Specimen #3 was run without pre-cycling.
[5] Pre-cycling significantly changes load curve characteristics. Specimen #1 was run with pre-cycling. Specimen #2 was run without pre-cycling.

TABLE 2

| Test Data | PET | Fluoropolymer Membrane | Non-woven |
|---|---|---|---|
| Drying Time | <30 min | 300 min | 1,273 min |
| Moisture Pick-up | 30% | 96% | 1,512% |
| Air Permeability | 1378 | 3.1 | 22 |
| Water Flow (liters/min) | 30 | 4.2 | 4.5 |
| Convective Cooling Test (deg. C./sec) | 2 | 38 | 4 |
| Apparent Density (method of Example 4) | 0.02 gm/cc | 0.02 gm/cc | 0.10 gm/cc |

We claim:

1. A padding or lining material for an orthopedic device used for bracing or fixation comprising a textile fabric, said textile fabric having a base plane, wherein a multiplicity of projections comprised of said textile fabric rises above said base plane, wherein said projections are resilient, returning substantially to their original shape after being compressed to 50% of their original height, said textile fabric comprising thermoplastic filaments wherein said thermoplastic filaments are monofils having a diameter of at least 0.1 mm.

2. The padding or lining material for an orthopedic device as recited in claim 1, said projections having apex points or flat tops, wherein said apex points or flat tops define a surface.

3. The padding or lining material for an orthopedic device as recited in claim 1, wherein said thermoplastic filaments consist essentially of a single thermoplastic polymer or copolymer.

4. The padding or lining material for an orthopedic device as recited in claim 3, wherein said thermoplastic polymer is poly(ethylene terephthalate).

5. The padding or lining material for an orthopedic device as recited in claim 1, wherein said filaments in said fabric cross over one another at intersections, wherein said filaments at said intersections are not bonded.

6. The padding or lining material according to claim 1, wherein said textile fabric comprises a bacteriacide.

7. The padding or lining material according to claim 1, wherein said material is in the form of a sheet stock.

8. A medical cast padding material comprising a textile fabric, said textile fabric having a base plane, wherein a multiplicity of projections comprised of said textile fabric rises above said base plane, wherein said projections are resilient, returning substantially to their original shape after being compressed to 50% of their original height, said textile fabric comprising thermoplastic filaments wherein said thermoplastic filaments are monofils having a diameter of at least about 0.1 mm.

9. The medical cast padding material as recited in claim 8, wherein said thermoplastic filaments consist essentially of a single thermoplastic polymer or coplymer.

10. The medical cast padding material as recited in claim 9, wherein said thermoplastic polymer has a melting temperature in the range of about 80° C. to about 375° C.

11. The medical cast padding material as recited in claim 9, wherein said thermoplastic polymer is poly(ethylene terephthalate).

12. The medical cast padding material as recited in claim 9, wherein said thermoplastic polymer is selected from the group consisting of polypropylene, nylon 6, nylon 66, and polyethylene.

13. The medical cast padding material as recited in claim 8, said projections having apex points or flat tops, wherein said apex points or flat tops define a surface.

14. The medical cast padding material as recited in claim 8, wherein said filaments in said fabric cross over one another at intersections, wherein said filaments at said intersections are not bonded.

15. The medical cast padding material as recited in claim 8, wherein the apparent density of said material is less than about 10% of the density of said thermoplastic fiber.

16. The medical cast padding material as recited in claim 8, wherein said fiber network also comprises depressions.

17. The medical cast padding material as recited in claim 8, said filaments having a diameter in the range of about 0.1 mm to about 0.25 mm.

18. The medical cast padding material as recited in claim 8, wherein said projections are about 4 to about 5 mm in height and about 9 to about 10 mm in diameter.

19. The medical cast padding material as recited in claim 8, wherein said textile fabric includes a bacteriacide.

20. A medical cast padding comprising the medical cast padding material recited in claim 8, for use with a rigid outer cast.

21. A medical cast padding material as recited in claim 8, wherein said material is pre-cut into a shape for use in a specific application, said material optionally including fasteners.

* * * * *

UNITED STATES PATENT AND TRADEMARK OFFICE
CERTIFICATE OF CORRECTION

PATENT NO. : 5,882,322
DATED : March 16,1999
INVENTOR(S) : KIm et al.

It is certified that error appears in the above-identified patent and that said Letters Patent is hereby corrected as shown below:

On the title page, insert
--[60]Related U.S. Application Data
   Provisional Application No. 60/009,057 Dec. 22,1995--.

Column 1, line 7, "Dec. 12,1995" should read --Dec.22,1995--.

Signed and Sealed this

Thirteenth Day of July, 1999

Q. TODD DICKINSON

Attest:

Attesting Officer

Acting Commissioner of Patents and Trademarks